(12) United States Patent
Joye

(10) Patent No.: US 6,541,428 B1
(45) Date of Patent: Apr. 1, 2003

(54) SULPHUR ORTHOPHOSPHATE COMPOSITIONS, PREPARATION AND USE

(75) Inventor: Jean-Luc Joye, Paris (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/700,416

(22) PCT Filed: May 15, 1998

(86) PCT No.: PCT/FR98/00974

§ 371 (c)(1),
(2), (4) Date: Mar. 5, 2001

(87) PCT Pub. No.: WO99/60002

PCT Pub. Date: Nov. 25, 1999

(51) Int. Cl.$^7$ ............... C10M 137/02; C10M 137/08; C10M 137/10; C10M 173/02

(52) U.S. Cl. ............. 508/329; 508/433; 558/183; 558/186

(58) Field of Search .................. 508/329; 558/183, 558/186

(56) References Cited

U.S. PATENT DOCUMENTS

| | | | | | |
|---|---|---|---|---|---|
| 3,723,578 A | * | 3/1973 | Eiseman, Jr. | ............... | 558/183 |
| 4,154,779 A | * | 5/1979 | Kreutzer | .................... | 558/183 |
| 4,177,154 A | * | 12/1979 | Chakrabarti | ............... | 508/433 |
| 4,511,480 A | * | 4/1985 | Outlaw et al. | ............. | 558/183 |
| 5,141,658 A | * | 8/1992 | DiBiase | ..................... | 508/433 |
| 5,306,436 A | * | 4/1994 | Born et al. | ................. | 558/186 |

FOREIGN PATENT DOCUMENTS

| | | |
|---|---|---|
| FR | 2252 402 | 6/1975 |
| FR | 2342 983 | 9/1977 |
| FR | 2758 561 | 7/1998 |

* cited by examiner

Primary Examiner—Jacqueline V. Howard
(74) Attorney, Agent, or Firm—Burns, Doane, Swecker & Mathis, L.L.P.

(57) ABSTRACT

The invention concerns alkoxylated sulfur alcohol orthophosphate compositions. It also concerns a method for preparing said compositions by sulphurizing alcohol orthophosphate composition. It further concerns the use of said alkoxylated sulphur alcohol orthophosphate compositions as multifunctional additives in lubricating or detergent aqueous formulations.

19 Claims, No Drawings

SULPHUR ORTHOPHOSPHATE COMPOSITIONS, PREPARATION AND USE

This application is a 371 of PCT/FR98/00974 May 15, 1998.

A subject-matter of the present invention is a composition formed of orthophosphates of alkoxylated sulphurized alcohols, a preparation process and their use as multifunctional additives in aqueous lubricating or detergent formulations.

Additives for lubricating formulations employed under very harsh conditions (shear, temperature) and comprising phosphorus and sulphur have been developed for some years. Such compounds make it possible to improve the antiwear and corrosion-inhibiting performances of the lubricating formulations proper. Mention may be made, among the compounds of this type of those disclosed in Patent FR 2 342 983. These compounds are sulphurized monoesters of monophosphoric acid.

These compounds, the advantage of which is not challenged here, nevertheless exhibit the disadvantage of not being water-soluble. Consequently, while their use does not present any difficulty for applications in oil-based lubricating compositions, it is necessary, in the case of use in aqueous formulations, as are, for example, metal cutting fluids, to combine them with appropriate surfactants. In this way, the operation is carried out in the presence of an emulsion. However, environmental restrictions are instead tending to limit the use of such compounds.

One of the objects of the present invention is thus to provide a composition which is both water-soluble or water-dispersible and which exhibits properties compatible in particular with use in aqueous lubricating fluids, without it being necessary to add surfactants.

Thus, a first subject-matter of the invention is alkoxylated sulphurized orthophosphate compositions (SOPC):

(i) comprising at least one compound of formula (I)

$(R^1-O)_3-P=O$ or a salt of this compound,
in which formula the $R^1$ radicals, which are identical or different, represent:
at least one of them, the $R^1-(O-X)_n-$ radical:
in which
$R^1$ is a hydrogen atom or a saturated or unsaturated, linear, branched or cyclic, hydrocarbonaceous radical comprising 1 to 30 carbon atoms,
X is a linear or branched alkylene radical comprising 2 to 4 carbon atoms,
n having a mean value of between 1 and 100, preferably 2 to 50.
a hydrogen atom,
a saturated or unsaturated, linear, branched or cyclic, hydrocarbonaceous radical comprising 1 to 30 carbon atoms,
at least one of the $R^1$ radicals of a molecule of compound of formula (I) being connected to another $R^1$ radical of another molecule of compound of formula (I) via one or more mono- or polysulphide bridges using S—C bonds;

(ii) and exhibiting a level of sulphur ranging from 1 to 50% by weight.

Another subject-matter of the invention is a process for the preparation of such compositions in which a sulphurization is carried out of an orthophosphate composition (OPC) comprising:

at least one orthophosphoric compound of formula (II):

$(R^2-O)_3-P=O$ or a salt of this compound,
in which formula the $R^2$ radicals, which are identical or different, represent:
at least one of them, the $R^2-(O-X)_n-$ radical:
in which
$R^2$ is a hydrogen atom or a saturated or unsaturated, linear, branched or cyclic, hydrocarbonaceous radical comprising 1 to 30 carbon atoms,
X is a linear or branched alkylene radical comprising 2 to 4 carbon atoms,
n having a mean value of between 1 and 100, preferably 2 to 50,
a hydrogen atom,
a saturated or unsaturated, linear, branched or cyclic, hydrocarbonaceous radical comprising 1 to 30 carbon atoms,
at least one alcohol of formula $R^2-(O-X)_n-OH$, in which $R^2$, X and n correspond to the above definition;
optionally at least one alcohol of formula $R^2-OH$, in which $R^2$ has the same definition as above;
and in which the iodine number of the $R^2$ radicals, measured on the alcohol of formula $R^2-OH$, is between 10 and 300, preferably between 50 and 120.

Finally, a subject-matter of the present invention is of use of these compounds as additives in aqueous formulations.

The composition according to the invention exhibits the advantage of introducing both phosphorus and sulphur and of being water-soluble or water-dispersable, without it being necessary to introduce a surfactant.

However, other advantages and objectives of the present invention will become more clearly apparent on reading the description and the example which will follow.

As was indicated previously, the composition according to the invention comprises orthophosphates of formula (I) $(R^1-O)_3-P=O$.

According to a more specific embodiment of invention, the $R^1$ radicals, which can be identical or different, are preferably linear or branched alkyl or mono- or polyunsaturated alkenyl radicals comprising 8 to 22 carbon atoms. Mention may in particular be made, as example of such radicals, of the stearyl, oleyl, linoleyl and linolenyl radicals.

The (SOPC) compositions according to the invention are particularly composed of molecules of orthophosphoric mono- or diesters, in the acid or salified form, or optionally of orthophosphoric triesters. It should be noted that they can be composed of a mixture of these species. And the (SOPC) compositions preferably comprise a mixture of orthophosphoric mono- and diesters. The (SOPC) compositions according to the invention can additionally comprise free phosphoric add. When it is present, the content of phosphoric acid, in the acid or salified form, can represent up to 10% by weight of the composition.

Mention may be made, among the salts of orthophosphoric compounds of formula (I), of those of the metals which appear from the columns IA, IIA, IB and VIII of the table of the Periodic Classification of the Elements. According to a particularly advantageous alternative form of the present invention, the salt of orthophosphoric compounds is a sodium, potassium, calcium, magnesium, iron, copper or zinc salt.

Mention may likewise be made, among the salts capable of being suitable, of salts of ammonium of formula —$NR_4+$, in which the R radicals, which are or are not identical, represent a hydrogen atom or an alkyl radical, optionally substituted by one or more hydroxyl groups, comprising 1 to 30, more particularly from 1 to 10, carbon atoms. Mention may be made, for example, of the ammonium deriving from ammonia, methylamine, ethylamine, propylamine, isopropylamine, monoethanolamine, diethanolamine, triethanolamine, monoethylethanolamine, from aminoethylethanolamine, diethylethanolamine or from aminomethylpropanolamine.

Up to 50% by weight of at least one alcohol of formula $R^1$—$(O$—$X)_n$—OH and optionally of at least one alcohol of formula $R^1$—OH, in which formulae $R^1$, X and n are defined as above, can also be present in said (SOPC) compositions.

In addition, it should be noted that the $R^1$ radicals can optionally be connected to other $R^1$ radicals present in the abovementioned alcohols or alternatively to $R^1$ radicals present in the orthophosphoric compounds of formula (I) via one or more mono- or polysulphide bridges using S—C bonds.

A second subject-matter of the invention is a process which makes it possible to prepare the sulphurized orthophosphate compositions (SOPC).

Said process consists in carrying, out a sulphurization of an orthophosphate composition (OPC) comprising:

at least one orthophosphoric compound of formula (II):

$$(R^2-O)_3-P=O$$

or a salt of this compound, in which formula the $R^2$ radicals, which are identical or different, represent:

at least one of them, the $R^2$—$(O$—$X)_n$—radical:
in which
$R^2$ is a hydrogen atom or a saturated or unsaturated, linear, branched or cyclic, hydrocarbonaceous radical comprising 1 to 30 carbon atoms,
X is a linear or branched alkylene radical comprising 2 to 4 carbon atoms,
n having a mean value of between 1 and 100, preferably 2 to 50,
a hydrogen atom,
a saturated or unsaturated, linear, branched or cyclic, hydrocarbonaceous radical comprising 1 to 30 carbon atoms,
at least one alcohol of formula $R^2$—$(O$—$X)_n$—OH, in which $R^2$, X and n correspond to the above definition;
optionally at least one alcohol of formula $R^2$—OH, in which $R^2$ at the same definition as above;
and in which the iodine number of the $R^2$ radicals, measured on the alcohols of formula $R^2$—OH, is between 10 and 300, preferably between 50 and 120.

According to a specific embodiment of invention, the $R^2$ radicals, which are identical or different, are linear or branched alkyl or mono- or polyunsaturated alkenyl radicals comprising 8 to 22 carbon atoms. Mention may be made, by way of example, of the stearyl, oleyl, linoleyl and linolenyl radicals.

The (OPC) composition to be sulphurized can be composed of molecules of monoester or of diester, in the acid or salified form, or optionally of triester or alternatively of a mixture of several of these species. The (OPC) composition preferably exhibits a mixture of monoester and of diester, in the acid or salified form.

Said (OPC) compositions can additionally comprise phosphoric acid, in the acid or salified form, representing up to 10% by weight of the composition.

Mention may be made, among the salts of orthophosphoric compounds of formula (II), of those of the metals which appear from the columns IA, IIA, IB and VIII of the table of the Periodic Classification of the Elements. According to a particularly advantageous alternative form of the present invention, the salt of orthophosphoric compounds is a sodium, potassium, calcium, magnesium, iron, copper or zinc salt.

Mention may likewise be made, among the salts capable of being suitable, of salts of ammonium of formula —$NR_4+$, in which the R radicals, which are or are not identical, represent a hydrogen atom or an alkyl radical, optionally substituted by one or more hydroxyl groups, comprising 1 to 10, more particularly from 1 to 6, carbon atoms. Mention may be made, for example, of the ammonium deriving from ammonia, trimethylamine, triethylamine, monoethanolamine, diethanolamine, triethanolamine, from aminoethylethanolamine or from aminomethylpropanolamine.

Furthermore, the composition to be sulphurized comprises at least one alcohol of formula $R^2$—$(O$—$X)_n$—OH and optionally at least one alcohol of formula $R^2$—OH. The content of these alcohols can represent up to 50% by weight of said composition.

The sulphurization operation is carried out in a known way with the aid of sulphur under an inert atmosphere, optionally in the presence of a sulphurization catalyst.

The amount of sulphur employed is generally from 1 to 50 parts by weight per 100 parts by weight of (OPC).

The temperature is conventionally of the order of 150° C. to 200° C.

The duration of the operation can be determined without difficulty by a person skilled in the art. By way of illustration it is between 1 and 4 hours approximately.

This sulphurization method is well known to a person skilled in the art, in particular for the sulphurization of triglycerides (Kirk-Othmer, Encyclopedia of Chemical Technology, Third Edition, Volume 22, page 258).

Orthophosphate compositions (OPC) which are well suited to the preparation of the sulphurized orthophosphate compositions (SOPC) forming the subject-matter of the invention are those resulting from the phosphation of at least one alcohol of formula $R^2$—$(O$—$X)_n$—OH; in which formula $R^2$, X and n have the same meaning as that given previously.

According to a specific embodiment, said alcohol originates from an alkoxylation of the alcohol of formula $R^2$—OH.

More particularly, the $R^2$ radicals, which are identical or different, are linear or branched alkyl or mono- or polyunsaturated alkenyl radicals comprising 8 to 22 carbon atoms. Mention may in particular be made, as example of such radicals, of the stearyl, oleyl, linoleyl and linolenyl radicals.

In addition, the iodine number of the $R^2$ radicals, measured on the alcohol of formula $R^2$—OH, is more particularly between 10 and 300, preferably between 50 and 120.

It should be noted that it would not be departing from the scope of the present invention to carry out the phosphation reaction on a mixture comprising at least alcohol indicated above and at least one other alcohol of formula $R^2$—OH, in which $R^2$ has the same meaning as that given above.

In such a case, the proportion of the latter alcohol ($R^2$—OH) with respect to the first ($R^2$—$(O$—$X)_n$—OH) is such that it makes it possible to access, after the phosphation and sulphurization reactions, a sulphurized orthophosphate compound corresponding to the formula (I).

More particularly, the content of alcohol of formula $R^2$—OH in the composition to be phosphated is such that it does not represent more than 20% by weight of the mixture of the two types of the abovementioned alcohols.

The phosphation methods are sell known to a person skilled in the art and, on this account, reference may be made, inter alia, to Applications FR 1 446 884 and EP 675 076.

The sulphurized orthophosphate compositions (SOPC) forming the subject-matter of the invention can be used in various applications because of their water-soluble or water-dispersible nature. In addition, they exhibit characteristics desired for lubricating applications (joint contribution of phosphorus and of sulphur) but they also have advantageous surface-active properties.

Thus, advantageously, they can be employed in particular as multifunctional additives in lubricating compositions in aqueous medium.

For example, they are advantageous if they are employed as antiwear, extreme-pressure and corrosion-inhibiting additives in aqueous lubricating formulations intended, inter alia, to be used in metallurgy. Metal cutting fluids are an illustration of applications of this type.

In such a case, said agents generally represent from 0.5 to 50% by mass of said formulations.

These formulations can also comprise other conventional extreme-pressure, antiwear, corrosion-inhibiting, surface-active, antioxidizing, biocidal, bacteriostatic agent or fungicidal additives and the like.

Finally, the sulphurized orthophosphate compositions (SOPC) according to the invention can advantageously be usable as surfactants in aqueous formulations intended to be used in industrial or household detergency.

A concrete but nonlimiting example of the invention will now be presented.

EXAMPLE

A commercial alkoxylated alkyl orthophosphate composition (OPC) Rhodafac PA 35® (sold by Rhodia Chimie), derived from the phosphation of a mixture of ethoxylated fatty alcohols R'—(O—$CH_2$—$CH_2$)$_5$—OH (based on stearyl, oleyl, linoleyl and linolenyl alcohols comprising on average 5 ethoxylated units), which mixture of alcohols exhibits an iodine number, calculated with respect to the R' radicals, of 70–75, is employed.

NMR (Nuclear Magnetic Resonance) analysis of this (OPC) composition gives the following information

RHODAFAC PA 35 ®

| Determination by: | $^{31}P$ NMR | $^{13}C$ NMR | $^{1}H$ NMR |
|---|---|---|---|
| Orthophosphoric compounds (molar %) | | | |
| inorganic phosphorus derivatives (phosphoric acid + traces of pyrophosphates) | 28 | | |
| Orthophosphoric monoesters | 55 | | |
| Orthophosphoric diesters | 17 | | |
| Orthophosphoric triesters | 0 | | |
| Molar % of free nonionic(*) | | 5 | |
| Mean length of R' chain (carbon atoms) | | | 17.3 |
| Mean unsaturation number per R' chain | | | 0.7 |
| Mean number of —O—$CH_2$—$CH_2$— units | | | 5.0 |

(*) corresponds to the following formula:
% $CH_2$—OH/(% $CH_2$—OH + % $CH_2$—OP).

95 g of this OPC composition are introduced into a 0.2 liter glass reactor equipped with a paddle stirrer and are heated to 140° C.

5 g of sulphur are subsequently added.

The mixture is heated to 150° C. and the maintained for 2 hours under an inert atmosphere at a temperature of the order of 180° C. (by virtue of the exothermicity of the system).

The $H_2S$ formed and the unreacted sulphur are removed by entrainment with air.

97.5 g of composition formed of orthophosphates of sulphurized ethoxylated alcohols (SOPO) exhibiting a level of sulphur of 2.5% by weight are obtained.

NMR (Nuclear Magnetic Resonance) analysis of this sulphurized composition (SOPC) gives the following information:

"Sulphurized" RHODAFAC PA 35 ®

| Determination by: | $^{31}P$ NMR | $^{13}C$ NMR | $^{1}H$ NMR |
|---|---|---|---|
| Orthophosphoric compounds (molar %) | | | |
| inorganic phosphorus derivatives (phosphoric acid + traces of pyrophosphates) | 37 | | |
| Orthophosphoric monoesters | 50 | | |
| Orthophospholic diesters | 13 | | |
| Orthophosphoric triesters | 0 | | |
| Molar % of free nonionic (*) | | 15 | |
| Mean length of R' chain (carbon atoms) | | | 17.3 |
| Mean unsaturation number per R' chain | | | 0.4 |
| Mean number of —O—$CH_2$—$CH_2$— units | | | 5.0 |

(*) corresponds to the following formula:
% $CH_2$—OH/(% $CH_2$—OH + % $CH_2$—OP).

The lower mean unsaturation number per R' chain of the (SOPC) composition with respect to that of the (OPC) composition is the proof of the presence of sulphur bridges in the (SOPC) composition.

The respective properties of multifunctional additives for a lubricating formulation of the starting Rhodafac PA 35® (OPC) composition and of the "sulphurized" Rhodafac PA 35® (SOPC) composition are compared using the Falex extreme-pressure (ASTM D3233-86) and antiwear (ASTM D2670-88) tests and the DIN 51360/2 corrosion-inhibiting test in aqueous medium.

1) Extreme-pressure and Antiwear Tests in Aqueous Medium

The (OPC) or (SOPC) composition to se tested is dissolved in water at different concentrations (see Tables 1 and 2) and then neutralized with triethanolamine "TEA".

The extreme-pressure and antiwear tests are subsequently carried out according to the above standards, without heating.

2) Corrosion-inhibiting Tests in Aqueous M$^2$edium

The (OPC) or (SOPC) composition to be tested is dissolved at 3% by weight and neutralized with 3% of triethanolamine.

The corrosion-inhibiting test is subsequently carried out according to the above standard.

The results obtained appear in Tables 1 and 2.

Analysis of these results shows that, with respect to the (OPC) composition, the (SOPC) composition exhibits:

improved properties as an extreme-pressure agent, at low concentration, whether in aqueous medium or in oil, greatly improved properties as an antiwear agent, and at very low concentration, equivalent properties as a corrosion-inhibiting agent.

TABLE 1

| Composition concentration In the medium % RHODAFAC PA 35 ® | Extreme-pressure Performance in kg ×0.4535 | Wear performance in mg | Corrosion inhibition grading |
|---|---|---|---|
| 0.1% 0.1% TFA concentration | 2000 | 71.7 | |
| 0.5% 0.5% TEA concentration | 2400 | 24.9 | |
| 1% 1% TEA concentration | 3800 | 21.8 | |
| 1.5% 1.5% TEA concentration | 4000 | — | |
| 2% 2% TEA concentration | 4300 | 7 | |
| 3% 3% TEA concentration | | | 0 |

TABLE 2

| Composition concentration in the medium % "Sulphurized" RHODAFAC PA 35 ® | Extreme-pressure performance in kg ×0.4535 | Wear performance in mg | Corrosion inhibition grading |
|---|---|---|---|
| 0.1% 0.1% TEA concentration | 2600 | 2.4 | |
| 0.5% 0.5% TEA concentration | 4100 | 1.3 | |
| 1% 1% TEA concentration | 4100 | 1.6 | |
| 1.5% 1.5% TEA concentration | 4500 | — | |
| 2 2% TEA concentration | 4500 | 2.6 | |
| 3% 3% TEA concentration | | | 0 |

What is claimed is:

1. A sulphurized orthophosphate composition (SOPC), comprising a mixture of sulphurized mono- and di-ester phosphates, in acid or salified form, and optionally tri-ester phosphates, wherein said mixture comprises:
   (i) at least one compound of formula $(1)(R^1-O)_3-P=O$ or a salt of this compound,
   in which formula the $R^1$ radicals, which are identical or different, represent:
   at least one of them, the $R^1-(O-X)_n$-radical:
      in which
      $R^1$ is a hydrogen atom or a saturated or unsaturated, linear, branched or cyclic, hydrocarbonaceous radical comprising 1 to 30 carbon atoms,
      X is a linear or branched alkylene radical comprising 2 to 4 carbon atoms,
      n having a mean value of between 1 and 100,
   a hydrogen atom,
   a saturated or unsaturated, linear, branched or cyclic, hydrocarbonaceous radical comprising 1 to 30 carbon atoms,
   at least one of the $R^1$ radicals of a molecule of compound of formula (1) being connected to another $R^1$ radical of another molecule of compound of formula (1) via one or more mono- or polysulphide bridges using S—C bonds;
   (ii) and in that it exhibits a level of sulphur ranging from 1 to 50% by weight.

2. A sulphurized orthophosphate composition (SOPC) as claimed in claim 1, wherein the $R^1$ radicals, which are identical or different, are linear or branched alkyl or alkenyl radicals comprising 8 to 22 carbon atoms.

3. A composition as claimed in claim 1, wherein the $R^1$ radicals, which are identical or different, comprise stearyl, oleyl, linoleyl or linolenyl radicals.

4. A sulphurized orthophosphate composition (SOPC) as claimed in claim 1, wherein in that said composition comprises phosphoric acid, in the acid or salified form, representing up to 10% by weight of the composition.

5. A sulphurized orthophosphate composition (SOPC) as claimed in claim 1, wherein in that the orthophosphoric compounds of formula (I) are in the form of salts of the metals which appear from the columns IA, IIA, IB and VII of the table of the Periodic Classification of the Elements or in the form of salts of ammonium of formula $-NR_4+$, in which the R radicals, which are or are not identical, represent a hydrogen atom or an alkyl radical, optionally substituted by one or more hydroxyl groups, comprising 1 to 30.

6. A sulphurized orthophosphate composition (SOPC) as claimed in claim 1, comprising up to 50% by weight of at least one alcohol of formula $R^1-(O-X)_n-OH$ and optionally of at least one alcohol of formula $R^1-OH$, in which formulae $R^1$, X and n are defined in accordance with the formula (I), it being possible for the $R^1$ radicals optionally to be connected to other $R^1$ radicals present in the above-mentioned alcohols or alternatively to $R^1$ radicals present in the orthophosphoric compounds of formula (I) via one or more mono- or polysulphide bridges using S—C bonds.

7. A process for the preparation of a sulphurized orthophosphate composition (SOPC) as claimed in claim 1, comprising carrying out a sulphurization of an orthophosphate composition (OPC) comprising:
   at least one orthophosphoric compound of formula (II):

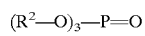

$(R^2-O)_3-P=O$ or a salt of this compound,
   in which formula the $R^2$ radicals, which are identical or different, represent:
   at least one of them, the $R^2-(O-X)_n-$ radical:
      in which
      $R^2$ is a hydrogen atom or a saturated or unsaturated, linear, branched or cyclic, hydrocarbonaceous radical comprising 1 to 30 carbon atoms,
      X is a linear or branched alkylene radical comprising 2 to 4 carbon atoms,
      n having a mean value of between 1 and 100,
   a hydrogen atom,
   a saturated or unsaturated, linear, branched or cyclic, hydrocarbonaceous radical comprising 1 to 30 carbon atoms,
   at least one alcohol of formula $R^2-(O-X)_n-OH$, in which $R^2$, X and n correspond to the above definition;
   optionally at least one alcohol of formula $R^2-OH$, in which $R^2$ at the same definition as above;
   and in which the iodine number of the $R^2$ radicals, measured on the alcohols of formula $R^2-OH$, is between 10 and 300.

8. The process as claimed in claim 7, wherein, in said (OPC) composition, the $R^2$ radicals, which are identical or different, are linear or branched alkyl or mono- or polyunsaturated alkenyl radicals comprising 8 to 22 carbon atoms.

9. The process as claimed in clam 8, wherein, the $R^2$ radicals, which are identical or different, comprises stearyl, oleyl, linoleyl or linolenyl radicals.

10. The process as claimed in claim 7, wherein the (OPC) composition to be sulphurized comprises molecules of monoester or of diester, in the acid or salified form, or optionally of triester or alternatively of a mixture of several of these species.

11. The process as claimed in claim 7, wherein said (OPC) compositions additionally comprise phosphoric acid, in the acid or salified form, representing up to 10% by weight of the composition.

12. The process as claimed in claim 7, wherein the orthophosphoric compounds of formula (II) are in the form of salts of the metals which appear from the columns IA, IIA, IB and VIII of the table of the Periodic Classification of the Elements or in the form of salts of ammonium of formula —$NR_4+$, in which the R radicals, which are or are not identical, represent a hydrogen atom or an alkyl radical, optionally substituted by one or more hydroxyl groups, comprising 1 to 30.

13. The process as claimed in claim 7, wherein the orthophosphate compositions (OPC) also comprise up to 50% by weight of at least one alcohol of formula $R^2$—(O—X)$_n$—OH and optionally of at least one alcohol of formula $R^2$—OH, $R^2$, X and n being defined in accordance with the formula (II).

14. The process as claimed in claim 7, wherein the sulphurization operation is carried out with the aid of sulphur under an inert atmosphere.

15. The process as claimed in claim 14, wherein a sulphurization catalyst is employed.

16. The process as claimed in claim 14, wherein the amount of sulphur employed is from 1 to 50 parts by weight per 100 parts by weight of the (OPC) composition.

17. An aqueous lubricating composition, comprising an effective amount of a sulphurized orthophosphate composition (SOPC), as defined in claim 1, as an antiwear, extreme-pressure or corrosion-inhibiting additive along with or additional ingredient.

18. An aqueous lubricating composition as claimed in claim 16, comprising 0.5 to 50% by mass of said formulations.

19. An aqueous composition which can be used in industrial detergency or in household detergency comprising an effective amount of a sulphurized orthophosphate composition (SPOPC), as defined in claim 1, as a surface-active agent along with acceptable carriers.

* * * * *